US008623916B2

(12) United States Patent
Redoules et al.

(10) Patent No.: US 8,623,916 B2
(45) Date of Patent: Jan. 7, 2014

(54) POLYUNSATURATED FATTY ACID AND DIOL ESTER AS AN ANTI-ACNE AGENT

(75) Inventors: Daniel Redoules, Toulouse (FR); Sylvie Daunes-Marion, Toulouse (FR); Marie-Françoise Aries, Escalquens (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 236 days.

(21) Appl. No.: 13/130,900

(22) PCT Filed: Dec. 21, 2009

(86) PCT No.: PCT/EP2009/067701
§ 371 (c)(1),
(2), (4) Date: May 24, 2011

(87) PCT Pub. No.: WO2010/072738
PCT Pub. Date: Jul. 1, 2010

(65) Prior Publication Data
US 2011/0230557 A1    Sep. 22, 2011

(30) Foreign Application Priority Data
Dec. 22, 2008   (FR) ..................... 08 58967

(51) Int. Cl.
*A61K 31/22*    (2006.01)
*A23D 9/00*    (2006.01)
*C11C 3/00*    (2006.01)

(52) U.S. Cl.
USPC .......................... 514/549; 554/172; 554/224

(58) Field of Classification Search
USPC .................... 514/549; 554/172, 224
See application file for complete search history.

(56) References Cited

U.S. PATENT DOCUMENTS

2008/0076699 A1    3/2008   Ley et al.

FOREIGN PATENT DOCUMENTS

| EP | 1902632 A1 | 3/2008 |
| WO | WO 96/34846 | 11/1996 |
| WO | WO 98/13330 A1 | 4/1998 |
| WO | WO 98/18751 | 5/1998 |
| WO | WO 01/38288 A1 | 5/2001 |
| WO | WO 2006/019186 A1 | 2/2006 |

OTHER PUBLICATIONS

Abd El All et al., "Immunohistochemical Expression of Interleukin 8 in Skin Biopsies from Patients with Inflammatory Acne Vulgaris," Diagnostic Pathology, vol. 2, No. 4, 2007, 6 pages.
Brown et al., "Acne Vulgaris," Seminar, The Lancet, vol. 351, Jun. 20, 1998, pp. 1871-1876.
Calder, "Polyunsaturated Fatty Acids, Inflammation, and Immunity," Lipids, vol. 36, No. 9, 2001, pp. 1007-1024.
Deangelis et al., "Isolation and Expression of a Malassezia Globosa Lipase Gene, LIP1," Journal of Investigative Dermatology, vol. 127, 2007, pp. 2138-2146.
Downie et al., "Peroxisome Proliferator-Activated Receptor and Farnesoid X Receptor Ligands Differentially Regulate Sebaceous Differentiation in Human Sebaceous Gland Organ Cultures In Vitro," British Journal of Dermatology, vol. 151, 2004, pp. 766-775.
Faergemann et al., "The Antimycotic Activity In Vitro of Five Diols,"Sabouraudia, vol. 18, 1980, pp. 287-293.
Faergemann et al., "The In Vitro Activity of Pentane-1,5-diol against Aerobic Bacteria. A New Antimicrobial Agent for Topical Usage?" Acta Derm Venereol, vol. 85, 2005, pp. 203-205.
Frankenfeld et al., "Preservation of Grain with Aliphatic 1,3-Diols and Their Esters," Journal of Agricultural and Food Chemistry, vol. 23, No. 3, 1975, pp. 418-425.
Harb et al., "Inhibitory Effect of 1,3-Butylene Glycol on Microorganisms," Drug & Cosmetic Industry, May 1976, pp. 40-41 and 136-137.
Ren et al., "Anti-Inflammatory Effect of α-Linolenic Acid and Its Mode of Action through the Inhibition of Nitric Oxide Production and Inducible Nitric Oxide Synthase Gene Expression via NF-κB . . . ," Journal of Agricultural and Food Chemistry, vol. 55, 2007, pp. 5073-5080 (published on web: Jun. 2, 2007).
Shalita, "The Integral Role of Topical and Oral Retinoids in the Early Treatment of Acne," Journal of the European Academy of Dermatology and Venereology, vol. 15, Supple. 3, 2001, pp. 43-49.
Sugiura et al., "Evidence That the Cannabinoid CB1 Receptor Is a 2-Arachidonoylglycerol Receptor," The Journal of Biological Chemistry, vol. 274, No. 5, Jan. 29, 1999, pp. 2794-2801.
International Search Report dated Feb. 19, 2010 for PCT/EP2009/067701.

*Primary Examiner* — Deborah D Carr
(74) *Attorney, Agent, or Firm* — Birch, Stewart, Kolasch & Birch, LLP.

(57) ABSTRACT

The present invention relates to compounds of the following formula (I): where n is an integer between 1 and 15, m is 0, 1, 2 or 3, and R is the hydrocarbon chain of a polyunsaturated fatty acid selected from among omega 3 and omega 6, as well as to pharmaceutical or cosmetic compositions containing same, to a method for preparing and using same, in particular for treating acne and seborrhoeic dermatitis.

19 Claims, 3 Drawing Sheets

POLYUNSATURATED FATTY ACID AND DIOL ESTER AS AN ANTI-ACNE AGENT

The present invention relates to esters of an alkanediol and a polyunsaturated fatty acid, more particularly an omega-3 or omega-6 fatty acid, as well as to pharmaceutical and cosmetic compositions containing same, to a method for preparing same and to the use of same, in particular to treat acne or seborrheic dermatitis.

Alkanediols are compounds used in numerous fields such as cosmetics and agri-foods. Their use as a preservative, by virtue of their bacteriostatic properties, can be cited in particular. Thus, alkanediols constitute a means to control fungal and bacterial colonization and help protect many cosmetic or agri-food products (Faergemann J, Fredriksson T. Sabouraudia: 1980; 18, 287-293). These diols have a broad spectrum of activity and are in particular effective with respect to species of fungi and Gram-positive bacteria (Harb N A, Toama M A. Drug Cosmet Ind: 1976; 118, 40). Moreover, the near absence of acquired resistance in microorganisms enables alkanediols to be important tools in the development of anti-resistance strategies, in particular with respect to Staphylococcus aureus (Faergemann J, Hedner T, Larsson P: 2005; 85, 203-205; WO 2004/112765). Finally, their very good tolerance enables them to be used frequently and at doses exceeding several percent.

In particular, 1,2-alkanediols have bacteriostatic activities and are widely used as preservatives (JP-A-51091327) or in the treatment of pathologies such as acne in which the microbial component plays a key role in etiology (U.S. Pat. No. 6,123,953). Other applications of 1,2-alkanediols are also described, such as protective properties with respect to body odors by virtue of their antiseptic (U.S. Pat. No. 5,516,510; WO 2003/000220) or antifungal (WO 2003/069994) effect. Similarly, combinations of 1,2-alkanediols with other compounds are described wherein the result is a synergistic antimicrobial effect. Thus, in this context, combinations to control microorganisms at the origin of body odors (US 2005/228032) or microorganisms involved in the formation of acne lesions (US 2007/265352, EP 1598064) have been claimed.

Polyunsaturated fatty acids (PUFAs) are divided into two categories: omega-3 ($\omega$-3) and omega-6 ($\omega$-6). Besides their metabolic effects, they are able to modify the expression of genes coding for intracellular proteins. Such gene effects of PUFAs seem to be carried out via nuclear receptors called PPARs (peroxisome proliferator-activated receptors). PPARs belong to the family of nuclear steroid hormone receptors. They form heterodimers with the retinoid X receptor (RXR) of retinoic acid and modulate gene expression. Thus, $\omega$-3 PUFAs would be negative regulators of the inflammatory response by inhibiting the NF-$\kappa$B activation pathway via the induction of the expression of I$\kappa$B$\alpha$, which is the major inhibiter of the NF-$\kappa$B pathway (Ren J and Chung S H. J Agric Food Chem. 2007 55:5073-80). Moreover, $\omega$-3 PUFAs have an inhibiting action on the synthesis of arachidonic acid to the benefit of the synthesis of docosahexaenoic and eicosapentaenoic acids (Calder P C. Lipids: 2001; 36, 1007-24).

During acne, excess sebum in the follicular infundibulum represents a favorable environment for colonization by *Propionibacterium acnes* (*P. acnes*). A correlation can thus be established between the degree of colonization by *P. acnes* of the pilosebaceous canal and the appearance of a microcomedo. Moreover, it has been shown that this colonization is greater in subjects with acne compared to healthy subjects (Brown S, Shalita A. Acne vulgaris. Lancet 1998; 351: 1871-6).

*P. acnes*, via receptors of the innate immune system, induce the production of NF-$\kappa$B-dependent proinflammatory cytokines such as IL-8, These mediators then influence in particular the migration of polynuclear neutrophils toward the site of inflammation, where their mission is to kill bacteria. This inflammatory response is normal and necessary for the elimination of the pathogen in the infected tissue. However, excessive and uncontrolled activation leads to inflammatory acne lesions. Thus, it has been shown that IL-8 level is correlated to the number of neutrophils mobilized in the inflammatory acne lesion (Abd El All H S et al. Diagn. Pathol. 2007; 2: 4).

Bacterial colonization in acne patients is most often associated with the appearance of inflammatory acne lesions: for example, a greater number of polymnuclear neutrophils and higher levels of IL-8 are found within the highly-colonized follicular canals compared to the lowly-colonized follicular canals of subjects without acne. The levels of these inflammatory markers appear correlated with bacterial load. But many questions remain unanswered such as the cause of colonization and the series of steps leading to lesion formation. In any event, the role of bacterial colonization as a factor in the progression of the disease is proven.

The current treatment for minor to moderate or inflammatory acne corresponds to a topical application of antibacterial active agents acting against colonization in particular by *P. acnes* in combination with anti-inflammatories (Shalita A., J. Eur. Acad. Dermatol. Venereol. 2001; 15: 43).

Treatments are generally initiated after the appearance of a certain number of inflammatory acne lesions.

One of the major problems of anti-acne therapy is to find an adapted treatment, which is to say one proportional to the severity of the acne, that is begun as soon as possible, which is to say as of the initial colonization, against the development of inflammatory acne lesions.

The Inventors thus discovered in a surprising way that esters of an alkanediol and a polyunsaturated fatty acid, and more particularly an omega-3 or omega-6 polyunsaturated fatty acid, have an antibacterial and anti-inflammatory action as of the initial colonization by *P. acnes* in the follicular canal, wherein this action is in addition proportional to the colonization.

Indeed, it turned out that alkanediol and PUFA esters are recognized and cleaved specifically by the bacterial (*P. acnes*) lipase, thus enabling, by cleavage of the ester bond, the release of the two active agents with complementary activities, namely the antibacterial diol, capable of controlling colonization by *P. acnes*, and the anti-inflammatory PUFA, which blocks the recruitment of neutrophils and thus the inflammatory cascade characteristic of acne. The release of these two active agents thus induces an adapted response, which is to say one proportional to the colonization by *P. acnes*, as of the initial colonization and thus blocks the development of this pathology responsible for the appearance of inflammatory acne lesions. In addition, since *P. acnes* bacteria are present in subjects who do not have acne lesions, these esters also make it possible to prevent aggravation of the acne lesion by acting as of the formation of the comedo and by inhibiting the inflammatory cascade characteristic of acne.

Such esters have already been described in the literature (WO 98/18751; Sugiura et al., J. Biol. Chem. 1999, 274(5), 2794-2801) but not for their biological properties.

Thus, the present invention relates to a compound of the following general formula (I):

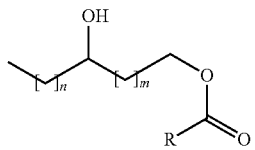
(I)

wherein:
n is an integer between 1 and 15, preferably between 1 and 10,
m is 0, 1, 2 or 3, and
R is the hydrocarbon chain of a polyunsaturated fatty acid selected from omega-3 and omega-6 polyunsaturated fatty acids.

In the context of the present invention, "polyunsaturated fatty acid" refers to a linear carboxylic acid ($R1CO_2H$) comprising from 10 to 28, preferably from 16 to 24, more preferably from 18 to 22, carbon atoms (including the carbon atom of the carboxylic acid function) and comprising at least 2, preferably 2 to 6, C=C double bonds, wherein said double bonds preferably have a cis configuration.

In the context of the present invention, "hydrocarbon chain of a polyunsaturated fatty acid" refers to the hydrocarbon chain (R1) linked to the acid function of the polyunsaturated fatty acid ($R1CO_2H$). R1 thus represents a linear hydrocarbon chain comprising from 9 to 27, preferably from 15 to 23, more preferably from 17 to 21, carbon atoms and comprising at least 2, preferably 2 to 6, C=C double bonds, wherein said double bonds preferably have a cis configuration. Thus, in the case of the linoleic acid of the following formula:

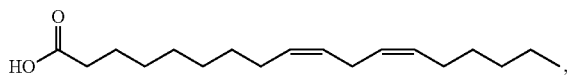

the hydrocarbon chain considered is the following chain:

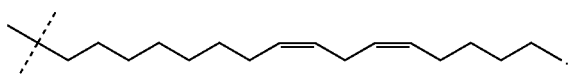

In the context of the present invention, "omega-3 fatty acid" refers to a polyunsaturated fatty acid, such as defined above, wherein the first double bond of the chain corresponds to the third carbon-carbon bond counting from the end opposite to the carboxylic acid function, as is illustrated in the case of the α-linolenic acid below:

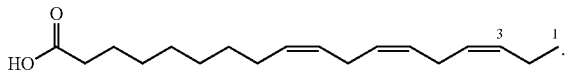

Said omega-3 fatty acids can be in particular α-linolenic acid, stearidonic acid, eicosatrienoic acid, eicosatetraenoic acid, eicosapentaenoic acid, docosapentaenoic acid, docosahexaenoic acid, tetracosapentaenoic acid and tetracosahexaenoic acid, and preferably it is α-linolenic acid or stearidonic acid, which have anti-inflammatory properties.

In the context of the present invention, "omega-6 fatty acid" refers to a polyunsaturated fatty acid, such as defined above, wherein the first double bond of the chain corresponds to the sixth carbon-carbon bond counting from the end opposite to the carboxylic acid function, as is illustrated in the case of the linoleic acid below:

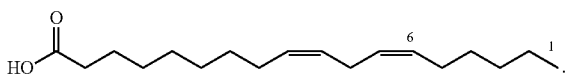 [SMILES: CCCCC/C=C\C/C=C\CCCCCCCC(=O)O]

Said omega-6 fatty acids can be in particular linoleic acid, γ-linolenic acid, eicosadienoic acid, dihomo-γ-linolenic acid, arachidonic acid, docosatetraenoic acid, docosapentaenoic acid, adrenic acid and calendic acid, and preferably it is linoleic acid, which has sebum control properties.

In particular, n can be 1, 2, 3, 4 or 5, preferably 5. Advantageously, n≥3 and preferably n≥5.

Advantageously, m is 0 or 1.

Advantageously, n+m≥3 and preferably n+m≥5.

Advantageously, the hydrocarbon chain comes from a polyunsaturated fatty acid selected from α-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, linoleic acid, γ-linolenic acid, eicosadienoic acid, dihomo-γ-linolenic acid, arachidonic acid, docosatetraenoic acid, docosapentaenoic acid, adrenic acid and calendic acid. Preferably, the polyunsaturated fatty acid will be selected from α-linolenic acid, stearidonic acid and linoleic acid, more preferably from α-linolenic acid and linoleic acid.

In particular, the compounds of the invention can be selected from the following molecules:

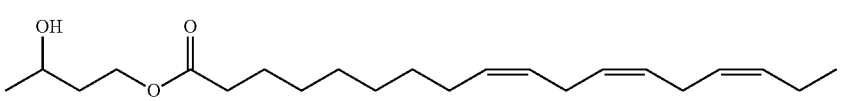
1

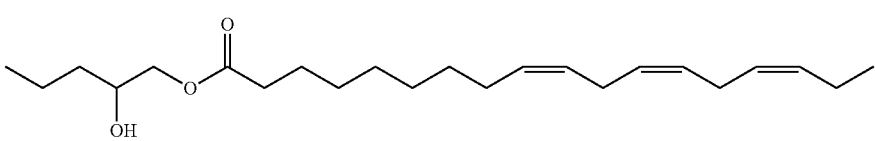
2

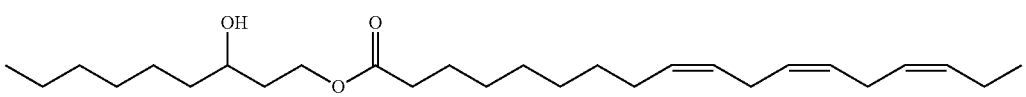
3

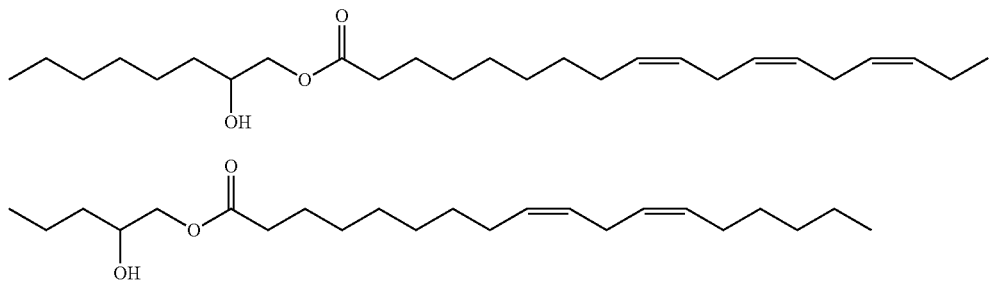

The present invention further relates to a compound of the formula (I) as defined above for the use of same as a drug, in particular intended to treat acne or seborrheic dermatitis.

The present invention further relates to the use of a compound of the formula (I) as defined above for the manufacture of a drug, in particular intended to treat acne or seborrheic dermatitis.

The present invention further relates to a method for treating acne or seborrheic dermatitis comprising the administration of an effective quantity of a compound of the formula (I) as defined above to a person in need thereof.

The present invention further relates to a pharmaceutical or cosmetic composition comprising at least one compound of the formula (I) as defined above in combination with at least one pharmaceutically or cosmetically acceptable excipient, adapted in particular to percutaneous administration.

In the present invention, "pharmaceutically or cosmetically acceptable" refers to that which is useful in the preparation of a pharmaceutical or cosmetic composition and is generally safe, non-toxic and neither biologically nor otherwise undesirable and is acceptable for therapeutic or cosmetic use, in particular by topical application.

The pharmaceutical or cosmetic compositions according to the invention can be provided in the forms commonly used for topical application, which is to say in particular lotions, foams, gels, dispersions, emulsions, shampoos, sprays, serums, masks, body milks or creams, with excipients that enable in particular cutaneous penetration in order to improve the properties and the accessibility of the active principle. Advantageously, said compositions are in the form of a cream.

Said compositions generally contain, in addition to the one or more compounds according to the present invention, a physiologically acceptable medium, in general water-based or solvent-based, for example based on alcohols, ethers or glycols. Said compositions can also contain surfactants, sequestrants, preservatives, stabilizers, emulsifiers, thickeners, gellants, humectants, emollients, trace elements, essential oils, fragrances, colorants, mattifiers, chemical or mineral filters, moisturizers or thermal waters, etc.

Said compositions can further contain other active principles leading to a complementary or possibly synergistic effect.

Advantageously, the compositions according to the present invention will comprise from 0.01% to 10% by weight, preferably from 0.1% to 1% by weight, of one or more compounds of the formula (I) compared to the total weight of the composition.

Said compositions are more particularly intended to treat acne or seborrheic dermatitis.

The present invention further relates to a method for the cosmetic treatment of acne or seborrheic dermatitis comprising the application on the skin of a cosmetic composition such as defined above.

The present invention further relates to a method for preparing a compound of the formula (I) as defined above by coupling a polyunsaturated fatty acid selected from omega-3 and omega-6 fatty acids, whose carboxylic acid function is in free or activated form, and a diol of the following formula (II):

wherein n is an integer between 1 and 15, preferably between 1 and 10, and m is 0, 1, 2 or 3.

In particular, n can be 1, 2, 3, 4 or 5, preferably 5. Advantageously, n≥1.3 and preferably n≥5.

Advantageously, m is 0 or 1.

Advantageously, n+m≥3 and preferably n+m≥5.

In the context of the present invention, "free form" means that the carboxylic acid function of the PUFA is not protected and is thus a $CO_2H$ group. The PUFA is thus of form $R1CO_2H$ such as previously defined.

In the context of the present invention, "activated form" refers to a carboxylic acid function that is modified so as to make it more active with respect to nucleophiles. Said activated forms are well known to those persons skilled in the art and can be in particular an acid chloride (COCl). The activated PUFA in the form of an acid chloride thus has formula R1COCl.

According to a first particular embodiment of the invention, the polyunsaturated fatty acid is used in its free acid form. In this case, the coupling reaction will be carried out in the presence of a coupling agent such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU), optionally combined with a coupling auxiliary such as N-hydroxysuccinimide (NHS), N-hydroxybenzotriazole (HOBt), 3,4-dihydro-3-hydroxy-4-oxo-1,2,3-benzotriazole (HOOBt), 1-hydroxy-7-azabenzotriazole (HOAt), dimethylaminopyridine (DMAP) or N-hydroxysulfosuccinimide (Sulfo-NHS). Advantageously, the coupling will be carried out in the presence of a carbodiimide (in particular DIC, DCC or EDC) and dimethylaminopyridine. Preferably, the coupling will be carried out in the presence of 1-(3-dimethylaminopropyl)-3-ethylcarbodiimide hydrochloride or diisopropylcarbodiimide and dimethylaminopyridine.

According to a second particular embodiment of the invention, the polyunsaturated fatty acid is used in its activated form, and more particularly in the form of an acid chloride. In this case, the coupling reaction will advantageously be carried out in the presence of pyridine and dimethylaminopyridine.

The present invention will be better understood in the light of the nonrestrictive examples which follow.

DESCRIPTION OF THE FIGURES

FIG. 4A corresponds to α-linolenic acid, FIG. 4B corresponds to stearidonic acid and FIG. 4C corresponds to linoleic acid.

Figure 1:
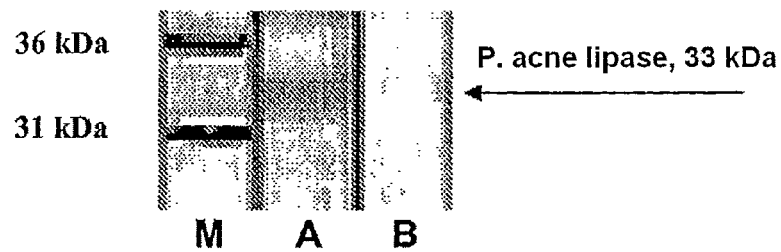
FIG. 1: Detection of *P. acnes* lipase (33 kDa) in inflammatory acne lesions (M corresponds to size markers; A corresponds to inflammatory acne lesions; B corresponds to comedos with no inflammation).

| ABBREVIATIONS USED: | |
|---|---|
| APCI | Atmospheric-pressure chemical ionization |
| MIC | Minimum inhibitory concentration |
| DPM | Disintegrations per minute |
| ESI | Electrospray ionization |
| HPLC | High-performance liquid chromatography |
| NMR | Nuclear magnetic resonance |
| Rf | Ratio to front |
| MS | Mass spectrum |
| CFU | Colony-forming unit |

EXAMPLE 1

Synthesis of Compounds of the Invention 1.1. General Method A: from an Unsaturated Fatty Acid The unsaturated fatty acid is put into solution in 20 ml anhydrous $CH_2Cl_2$ under circulating $N_2$. A carbodiimide (coupling agent) (1.1 eq) and dimethylaminopyridine (0.5 eq) are then added directly. After stirring the medium at room temperature for 5-10 minutes, the diol (5 eq) is added. The medium is stirred vigorously for 18 hours, under $N_2$, away from light. The organic phase is then extracted with $CH_2Cl_2$ and then washed with a saturated NaCl solution, dried on $MgSO_4$, filtered and concentrated.

The crude product is a yellow oil which is purified by open column chromatography using silica gel (Ø: 22×3.5 cm) and $CHCl_3$ as solvent.

The following three products were prepared according to method A with diisopropylcarbodiimide as coupling agent.

3-Hydroxybutyl
(9Z,12Z,15Z)-octadeca-9,12,15-trienoate ($C_{22}H_{38}O_3$) (3-hydroxybutyl α-linolenate)

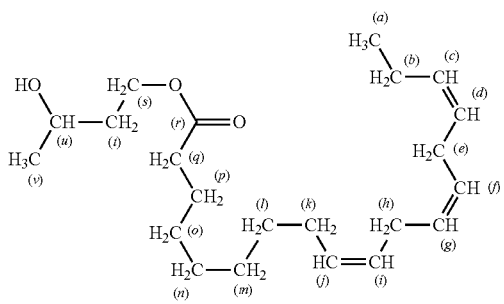 [SMILES: CC/C=C\C/C=C\C/C=C\CCCCCCCC(=O)OCCC(C)O]

Purification conditions: elution gradient: $CHCl_3$/AcOEt: 95/5 then $CHCl_3$/AcOEt: 9/1

Translucent oil (yield: 69%)

Rf ($CHCl_3$/AcOEt: 9/1)=0.5

NMR ($^1$H, $CDCl_3$) δ (ppm): 0.98 (t, 3H, $CH_{3\,(a)}$); 1.22 (d, 3H, $CH_{3\,(v)}$); 1.31 (m, 8H, $CH_{2\,(o,n,m,l)}$); 1.6 (m, 2H, $CH_{2\,(p)}$); 1.8 (m, 2H, $CH_{2\,(t)}$); 2.1 (m, 4H, $CH_{2\,(k,b)}$); 2.3 (t, 2H, $CH_{2\,(q)}$); 2.8 (m, 4H, $CH_{2\,(h,e)}$); 3.85 (m, 1H, $CH_{(u)}$); 4.1-4.3 (m, 2H, $CH_{2\,(s)}$); 5.4 (m, 6H, $CH_{(c,d,f,g,i,j)}$).

NMR ($^{13}$C, $CDCl_3$) δ (ppm): 14.24 ($CH_{3\,(a)}$); 20.46 ($CH_{2\,(b)}$); 23.42 ($CH_{3\,(v)}$); 25.01 ($CH_{2\,(p)}$); 25.5 ($CH_{2\,(e)}$); 25.59 ($CH_{2\,(h)}$); 27.16 ($CH_{2\,(k)}$); 29.06 ($CH_{2\,(o,n)}$); 29.07 ($CH_{2\,(m)}$); 29.53 ($CH_{2\,(l)}$); 34.3 ($CH_{2\,(q)}$); 38.1 ($CH_{2\,(t)}$); 61.51 ($CH_{2\,(s)}$); 64.89 ($CH_{(u)}$); 127.08 ($CH_{(c)}$); 127.6 ($CH_{(j)}$); 128.22 ($CH_{(f)}$); 128.26 ($CH_{(g)}$); 130.22 ($CH_{(i)}$); 131.93 ($CH_{(d)}$); 174.2 ($C=O_{(r)}$).

MS: ESI+ [M+H]$^+$=351.2 (100%); [M+Na]$^+$=373.3 (48%)
APCI+ [M+H]$^+$=351.2 (calculated M=350.2)

2-Hydroxypentyl
(9Z,12Z,15Z)-octadeca-9,12,15-trienoate ($C_{23}H_{40}O_3$) (2-hydroxypentyl α-linolenate)

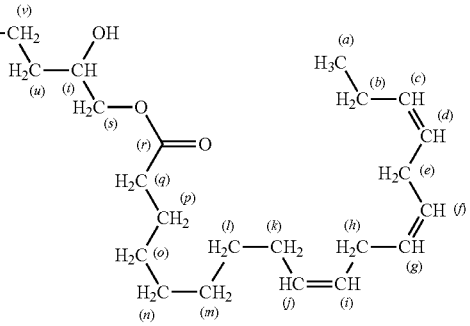

Purification conditions: CHCl$_3$/AcOEt: 98/2

Translucent oil (yield: 45%)

Rf (CHCl$_3$/AcOEt: 97/3)=0.58

NMR ($^1$H, CDCl$_3$) δ (ppm): 1 (m, 6H, CH$_{3\ (w,\ a)}$); 1.25 (m, 10H, CH$_{2\ (o,\ n,\ m,\ l,\ v)}$); 1.5 (m, 4H, CH$_{2\ (p,\ u)}$); 1.65 (m, 4H, CH$_{2\ (b,\ k)}$); 2.1 (m, 2H, CH$_{2\ (e)}$); 2.4 (t, 2H, CH$_{2\ (q)}$); 2.8 (m, 2H, CH$_{2\ (h)}$); 3.9 (m, 1H, CH$_{(t)}$); 4.1-4.3 (m, 2H, CH$_{2\ (s)}$); 5.4 (m, 6H, CH$_{(d,\ d,\ f,\ g,\ i,\ j)}$).

NMR ($^{13}$C, CDCl$_3$) δ (ppm): 14.2 (CH$_{3\ (a,\ w)}$); 18.6 (CH$_{2\ (v,\ b)}$); 25.5 (CH$_{2\ (p)}$); 25.5 (CH$_{2\ (p)}$); 27.16 (CH$_{2\ (e)}$); 28.9 (CH$_{2\ (h)}$); 29.1 (CH$_{2\ (k)}$); 29.4 (CH$_{2\ (o,\ n)}$); 29.5 (CH$_{2\ (m)}$); 34.17 (CH$_{2\ (q)}$); 35.41 (CH$_{2\ (u)}$); 68.53 (CH$_{(t)}$); 69.76 (CH$_{2\ (s)}$); 128.22 (CH$_{(c)}$); 129.58 (CH$_{(j)}$); 130.22 (CH$_{(f)}$ CH$_{(g)}$); 130.81 (CH$_{(i)}$); 131.93 (CH$_{(d)}$); 174.05 (C=O$_{(r)}$).

MS: APCI+ [M+H]$^+$=365.1 (calculated M=364.3)

3-Hydroxynonyl
(9Z,12Z,15Z)-octadeca-9,12,15-trienoate (C$_{27}$H$_{48}$O$_3$) (3-hydroxynonyl α-linolenate)

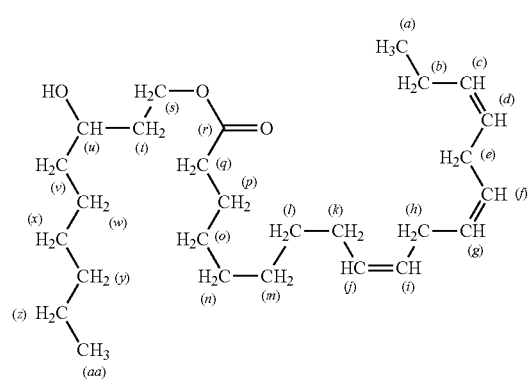 [SMILES: CC/C=C\C/C=C\C/C=C\CCCCCCCC(=O)OCCC(O)CCCCCC]

Purification conditions: CHCl$_3$/AcOEt: 96/4

Translucent oil (yield 73%)

Rf (CHCl$_3$/AcOEt: 97/3)=0.64

NMR ($^1$H, CDCl$_3$) δ (ppm): 0.95 (m, 3H, CH$_{3\ (aa)}$) 1 (m, 3H, CH3$_{(a)}$); 1.4 (m, 16H, CH$_{2\ (o,\ n,\ m,\ l,\ w,\ x,\ y,\ z)}$); 1.5 (m, 2H, CH$_{2\ (v)}$); 1.6-1.8 (m, 4H, CH$_{2\ (p,\ t)}$); 2 (m, 4H, CH$_{2\ (k,\ b)}$); 2.3 (t, 2H, CH$_{2\ (q)}$); 2.8 (m, 4H, CH$_{2\ (h,\ e)}$); 3.7 (m, 1H, CH$_{(u)}$); 4.1-4.3 (m, 2H, CH$_{2\ (s)}$); 5.4 (m, 6H, CH$_{(d,\ d,\ f,\ g,\ i,\ j)}$).

NMR ($^{13}$C, CDCl$_3$) δ (ppm): 14 (CH$_{3\ (a,\ aa)}$); 20.4 (CH$_{2\ (b)}$); 22.5 (CH$_{2\ (z)}$); 25.09 (CH$_{2\ (p)}$); 25.26 (CH$_{2\ (w)}$); 25.58 (CH$_{2\ (e,\ h)}$); 27.17 (CH$_{2\ (k)}$); 29.06-29.3 (CH$_{2\ (x,\ o,\ n,\ m,\ l)}$); 31.7 (CH$_{2\ (y)}$); 34.5 (CH$_{2\ (q)}$); 37.45 (CH$_{2\ (t)}$); 37.58 (CH$_{2\ (v)}$; 61.59 (CH$_{2\ (s)}$); 68.72 (CH$_{(u)}$); 127.08 (CH$_{(c)}$); 127.71 (CH$_{(j)}$); 128.21 (CH$_{(f)}$); 128.26 (CH$_{(g)}$); 130.22 (CH$_{(i)}$); 131.94 (CH$_{(d)}$); 174.9 (C=O$_{(r)}$).

MS: ESI+ [M+H]$^+$=421.1 (100%); [M+Na]$^+$=443.1 (92%)

The following product was prepared according to method A with 1-(3-dimethylaminopropyl)-3-ethylcarbodiimide hydrochloride as coupling agent.

2-Hydroxyoctyl
(9Z,12Z,15Z)-octadeca-9,12,15-trienoate (C$_{26}$H$_{46}$O$_3$) (2-hydroxyoctyl α-linolenate)

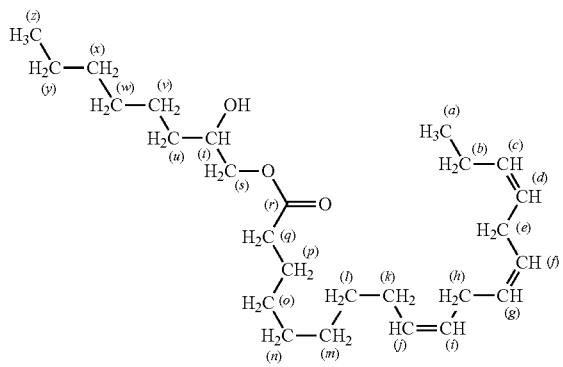 [SMILES: CC/C=C\C/C=C\C/C=C\CCCCCCCC(=O)OCC(O)CCCCCC]

Purification conditions: CHCl$_3$/AcOEt: 98/2
Translucent oil (yield 37%)
Rf (CHCl$_3$/AcOEt: 98/2)=0.72
NMR ($^1$H, CDCl$_3$) δ (ppm): 0.88 (m, 3H, CH3$_{(z)}$); 0.97 (t, 3H, CH$_{3\ (a)}$); 1.31 (m, 16H, CH$_{2\ (o,\ n,\ m,\ l,\ v,\ w,\ x,\ y)}$); 1.47 (m, 2H, CH$_{2\ (u)}$); 1.65 (m, 2H, CH$_{2\ (p)}$); 2.02 (m, 4H, CH$_{2\ (b,\ k)}$); 2.4 (t, 2H, CH$_{2\ (q)}$); 2.8 (m, 4H, CH$_{2\ (e,\ h)}$); 3.9 (m, 1H, CH$_{(t)}$); 4.1-4.3 (m, 2H, CH$_{2\ (s)}$); 5.4 (m, 6H, CH$_{(c,\ d,\ f,\ g,\ i,\ j)}$).

NMR ($^{13}$C, CDCl$_3$) δ (ppm): 14.2 (CH$_{3\ (a,\ w)}$); 18.6 (CH$_{2\ (v,\ b)}$); 22.7 (CH$_{2\ (y)}$); 25.5 (CH$_{2\ (p)}$); 25.5 (CH$_{2\ (p)}$); 27.16 (CH$_{2\ (e)}$); 28.9 (CH$_{2\ (h)}$) 29.1 (CH$_{2\ (k)}$); 29.4 (CH$_{2\ (o,\ n,)}$); 29.5 (CH$_{2\ (m)}$); 29.9 (CH$_{2\ (w)}$); 31.7 (CH$_{2\ (x)}$); 34.17 (CH$_{2\ (q)}$); 35.41 (CH$_{2\ (u)}$); 68.53 (CH$_{(t)}$); 69.76 (CH$_{2\ (s)}$); 128.22 (CH$_{(c)}$); 129.58 (CH$_{(j)}$); 130.22 (CH$_{(f)}$ CH$_{(g)}$); 130.81 (CH$_{(i)}$); 131.93 (CH (d)); 174.05 (C=O$_{(r)}$).
MS: APCI+ [M+H]$^+$=407.3 (calculated M=406.34)

1.2. General Method B: from a Polyunsaturated Fatty Acid Chloride

Linoleoyl chloride (6.7×10$^{-3}$ mol) and dimethylaminopyridine (DMAP) (0.1 eq) are added, under circulating nitrogen, to a solution of diol (5 eq) in pyridine (20 ml). After vigorous stirring for 18 hours under N$_2$, at room temperature and away from light, the reaction medium is reduced dry.

The organic phase is then extracted with AcOEt and then washed with H$_2$O and NH4$^+$Cl$^-$, dried on MgSO$_4$, filtered and concentrated.

The crude product is a brown oil which is purified by open column chromatography using silica gel (Ø: 22×3.5 cm) and CHCl$_3$ as solvent.

The following product was prepared according to method B with pentylene glycol as the diol.

2-Hydroxypentyl (9Z,12Z)-octadeca-9,12-dienoate (C$_{23}$H$_{42}$O$_3$) (2-hydroxypentyl linoleate)

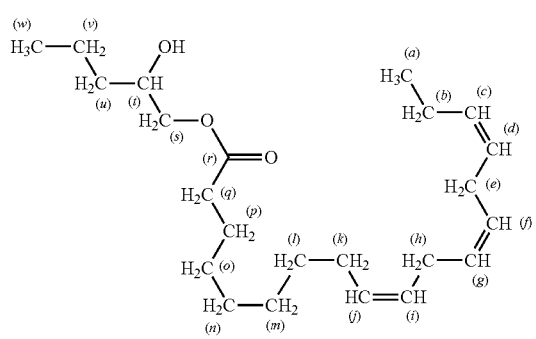 [SMILES: CC/C=C\C/C=C\C/C=C\CCCCCCCC(=O)OCC(O)CCC]

Purification conditions: CHCl$_3$/AcOEt: 98/2

Translucent oil

Rf (CHCl$_3$/AcOEt: 98/2)=0.54

NMR ($^1$H, CDCl$_3$) δ (ppm): 0.9 (m, 6H, CH$_{3\ (a,\ w)}$) 1.3 (m, 16H, CH$_{2\ (o, n, m, l, b, c, d, v)}$); 1.45 (m, 2H, CH$_{2\ (u)}$); 1.65 (m, 2H, CH$_{2\ (p)}$); 2 (m, 4H, CH$_{2\ (k, e)}$); 2.3 (t, 2H, CH$_{2\ (q)}$); 2.8 (m, 2H, CH$_{2\ (h)}$); 3.8 (m, 1H, CH$_{(t)}$); 4.1-4.3 (m, 2H, CH$_{2\ (s)}$); 5.4 (m, 4H, CH$_{(f, g, i, j)}$).

NMR ($^{13}$C, CDCl$_3$) δ (ppm): 14.2 (CH$_{3\ (a,\ w)}$); 18.6 (CH$_{2\ (v)}$); 22.6 (CH$_{2\ (b)}$); 25 (CH$_{2\ (p)}$); 25.6 (CH$_{2\ (h)}$); 27.2 (CH$_{2\ (e,\ h)}$); 29 (CH$_{2\ (o)}$); 29.1 (CH$_{2\ (n)}$); 29.3 (CH$_{2\ (d)}$); 29.4 (CH$_{2\ (m)}$); 29.6 (CH$_{2\ (l)}$); 31.4 (CH$_{2\ (c)}$); 34.1 (CH$_{2\ (q)}$); 36.2 (CH$_{2\ (u)}$); 69 (CH$_{2\ (s)}$); 70 (CH$_{(t)}$); 127.78 (CH$_{(g)}$); 127.91 (CH$_{(i)}$); 129.94 (CH$_{(f)}$); 130.22 (CH$_{(j)}$); 174.05 (C=O$_{(r)}$).

MS: ESI+ [M+H]$^+$=367.3 (100%); [M+Na]$^+$=389.3 (80%)

EXAMPLE 2

Composition According to the Invention

A formulation according to the invention, in cream form, with the following composition (the quantities are given in weight percentages compared to the total weight of the composition):

| Quantity | Compound | Function |
|---|---|---|
| 3 | Glycerin | Humectant |
| 0.1 | Disodium EDTA* | Sequestrant |
| 0.35 | Phenoxyethanol | Preservative |
| 1 | Polyacrylate-13; Polyisobutene; Polysorbate 20; water (mixture sold under the name Sepiplus ® 400 by SEPPIC) | Gellant and stabilizer |
| 4 | Glyceryl stearate; PEG-100 stearate (mixture sold under the name Simulsol ® 165 by SEPPIC) | Emulsifier |
| 1 | Cetyl alcohol | Consistency factor |
| 5 | Cyclopentasiloxane | Emollient |
| 3 | Glyceryl tri-2-ethylhexanoate | Emollient |
| 2 | Dicaprylyl carbonate | Emollient |
| 1 | Diol and PUFA ester according to the invention | Anti-acne agent |
| 0.27 | Chlorphenesin | Preservative |
| 2 | Polymethyl methacrylate | Mattifying powder |
| 0.1 | Fragrance | Fragrance |

*EDTA: ethylenediaminetetraacetic acid

EXAMPLE 3

Results of Biological Tests 3.1. Study of the Action of *P. acnes* Lipase on the Compounds of the Invention First, it was shown by Western blot that the *P. acnes* lipase is strongly induced in the inflammatory lesions of subjects with acne compared to samples taken from healthy subjects (see FIG. 1).

Second, the action of recombinant *P. acnes* lipase on the compounds of the invention was studied as described below.

The enzymatic reaction was carried out by incubating the substrate at the desired concentration (500 μM) in TRIS buffer (left at room temperature for 1 h before the tests began) and then initiated the reaction by adding the enzyme and incubating at 37° C. The tests are carried out in 2 ml amber glass vials. A control is carried out by not adding the enzyme in order to evaluate the possible spontaneous hydrolysis of the substrate in the buffer. A 10 μl sample is taken at each desired time during the reaction and then frozen to quench the reaction. The linolenic acid released is then derivatized with anthryldiazomethane (ADAM) which forms a fluorescent complex with the fatty acid. The product formed is separated by HPLC and then quantified using a standard range of commercial linolenic acid derivatized under the same conditions.

Figure 2:
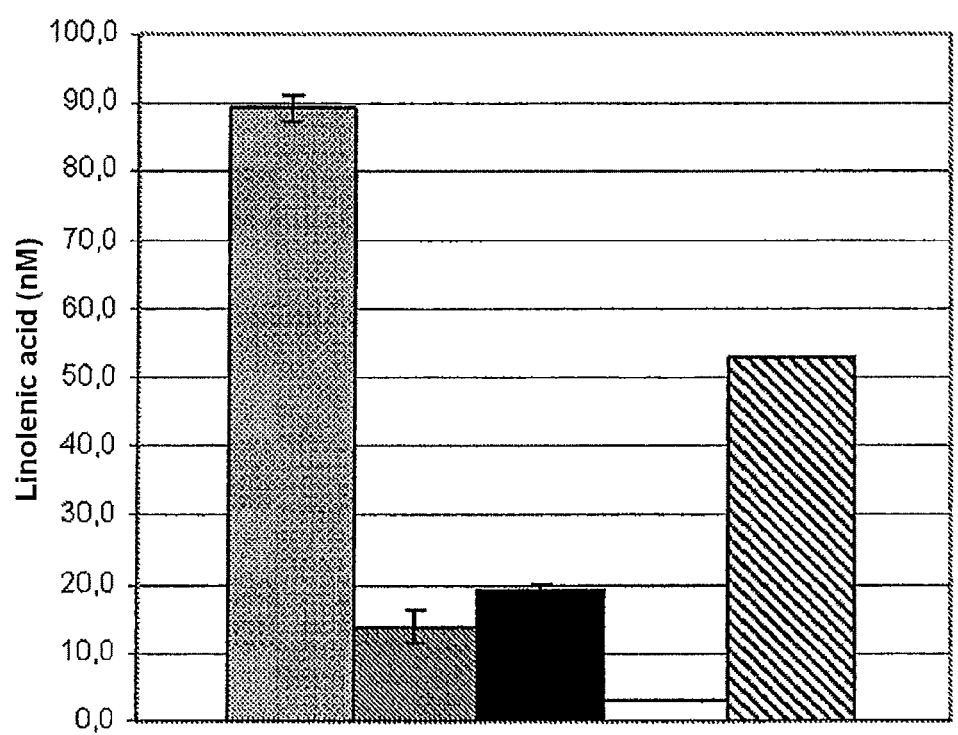
FIG. 2: Study of the hydrolysis of the esters of the invention by recombinant *P. acnes* lipase after 2 h of incubation. The light gray column represents the results obtained with 3-hydroxybutyl α-linolenate, the dark gray column represents the results obtained with 2-hydroxypentyl α-linolenate, the black column represents the results obtained with 2-hydroxyoctyl α-linolenate, the white column represents the results obtained with 3-hydroxynonyl α-linolenate and the hatched column represents the results obtained with glyceryl trilinolenate.

As shown in FIG. 2, the compounds of the invention give rise to a hydrolysis reaction in the presence of *P. acnes*, since the formation of α-linolenic acid is observed.

Thus, hydrolysis of the compounds of the invention by *P. acnes* releases both the diol and the PUFA. Expression of the lipase is thus a necessary condition to observe the cleavage of compounds of the invention and thus to obtain a therapeutic effect. In addition, since the *P. acnes* lipase is essentially present in subjects with acne, as shown in FIG. 1, the compounds of the invention should enable an adapted response for each person.

3.2. Study of the Antibacterial Activity of the Diols Obtained after Hydrolysis of the Compounds of the Invention Said diols are of the following general formula (II):

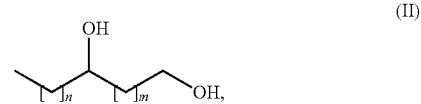

(II)

wherein n is an integer between 0 and 15 and m is 0, 1, 2 or 3.

Tests were carried out with eight microbial strains using the dilution method described below.

Minimum inhibitory concentrations (MICs) are determined using a micromethod in liquid medium. Successive 1/2 dilutions of the test products in culture medium (Trypcase Soy Broth) are carried out in 96-well microplates in a final volume of 0.1 ml. The wells are inoculated with 0.01 ml of the bacterial suspensions titrated at roughly 1×10$^7$ CFU/ml. The microplates are incubated in optimal growth conditions and the MIC is read visually.

Table 1 below presents the results obtained with various diols. The columns labeled "BS" represent the bacteriostatic activity and the columns labeled "BC" represent the bactericidal activity of the diols (1% corresponds to a concentration of 10 mg/ml).

TABLE I

| Bacterium | 1,3-Butanediol | | 1,2-Pentanediol | | 1,2-Octanediol | | 1,3-Nonanediol | |
|---|---|---|---|---|---|---|---|---|
| | BS | BC | BS | BC | BS | BC | BS | BC |
| Staphylococcus aureus | 20% | >20% | 20% | 20% | 0.312% | 0.312% | 0.312% | 0.312% |
| Staphylococcus epidermis | 10% | 20% | 10% | 10% | 0.312% | 0.312% | 0.312% | 0.312% |
| P. acnes | 10% | 20% | 5% | 20% | 0.312% | 0.312% | 0.156% | 0.312% |
| Pseudomonas aeruginosa | 10% | 20% | 5% | 10% | 0.312% | 0.312% | 0.625% | 0.625% |
| Escherichia coli | 10% | 20% | 5%-10% | 20% | 0.156% | 0.156% | 0.156% | 0.625% |
| Candida albicans | 10% | 10% | 5% | 5% | 0.156% | 0.312% | 0.156% | 0.156% |
| Aspergillus niger | 10% | >20% | 5% | 20% | 0.156% | 0.625% | 0.078% | 0.625% |
| M. furfur | 10% | 20% | 5% | 10% | 0.156% | 0.312% | 0.156% | 0.312% |

The antibacterial effect observed is consistent with the literature: namely, the activity is in relation to the length of the diol chain (Frankenfeld J W, Mohan R R, Squibb R L. J Agric Food Chem. 1975; 23: 418-425). Thus, 1,3-nonanediol and 1,2-octanediol are bacteriostatic and bactericidal (Gram-positive, Gram-negative, fungal) at concentrations ranging from 6.25 mg/ml to 0.78 mg/ml. It should be noted that the nonane derivative appears to have the most marked activity for the P. acnes strain with in particular a bacteriostatic and bactericidal effect found at 1.56 mg/ml and 3.12 mg/ml, respectively.

After each time of contact (contact times tested: 5 min, 15 min, 30 min and 60 min), residual bacteria are counted by taking a 1 ml aliquot neutralized by 9 ml Trypcase Soy Broth and 10% Polysorbate 80.

Counting is carried out by adding 1 ml neutralized mixture and four 1/10 serial dilutions to the corresponding agar plates.

The agar plates are incubated at 36° C.±1° C. in aerobic atmosphere for S. aureus and anaerobic atmosphere for P. acnes (Generbag anaer, Biomerieux) for 72 hours and then the CFUs are counted.

Table 2 below presents the results obtained.

TABLE 2

| | | Staphylococcus aureus Log R | | | | Propionibacterium acnes Log R | | | |
|---|---|---|---|---|---|---|---|---|---|
| Concentration | pH | 5 min | 15 min | 30 min | 60 min | 5 min | 15 min | 30 min | 60 min |
| 1% | 7 | >5.3 | >5.3 | >5.3 | >5.3 | >5 | >5 | >5 | >5 |
| 0.5% | 7 | 0.4 | 0.1 | 0.2 | 0.5 | 0.2 | 0.7 | 1.8 | 3 |
| Negative control: 1% Polysorbate 20 excipient | 6.5 | 0 | 0 | 0 | 0.1 | 0 | 0 | 0.2 | 0.3 |

3.3. Study of the Kinetics of the Antibacterial Activity of 1,2-octanediol

The kinetics of the antibacterial activity of 1,2-octanediol were studied by evaluating the lethality of the bacteria over time by counting residual colony-forming units (CFUs) after contact of the test solution with the bacterial suspension.

The bacterial strains used are: Staphylococcus aureus ATCC6538 and Propionibacterium acnes ATCC6919. The culture medium used for Staphylococcus aureus ATCC6538 is Trypcase Soy Agar whereas the culture medium used for Propionibacterium acnes ATCC6919 is Schaedler agar. Stock solutions containing 1% and 0.5% 1,2-octanediol are prepared extemporaneously in 1% Polysorbate 20 (qsp WFI) and then adjusted to pH 7 with 0.1 N NaOH solution.

A volume of 5 ml of each stock solution is inoculated with 50 µl bacterial suspension titrated at roughly 1×10$^8$ CFU/ml.

with R meaning "reduction". It refers to the ratio between the number of inoculated bacteria and the number of residual bacteria after contact of the test solution with the bacterial suspension.

The bactericidal action of the octanediol was examined on two bacterial species (P. acnes, S. aureus) at the two following concentrations of 0.5% and 1%. At physiological pH and at the lowest concentration (0.5%), a decrease greater than 99.9% of the population of P. acnes in particular is observed after one hour of contact.

3.4. Study of the Anti-Inflammatory Activity of PUFAs Obtained After Hydrolysis of the Compounds of the Invention The anti-inflammatory potential of the PUFAs was tested on human keratinocytes (HaCaT) stimulated by PMA/A23187. The results obtained are presented in FIGS. 3, 4A, 4B and 4C.

The changes induced by these PUFAs are evaluated on the production of eicosanoids and an inflammatory cytokine, interleukin 8, during an inflammatory process triggered by PMA/A23187.

Study of IL-8 Secretion (FIG. 3):

HaCaT cells are incubated on 96-well plates for 24 h in the presence of PUFAs, rinsed and then stimulated by PMA/A23187. The supernatants are recovered after 6 h of stimulation and IL-8 is quantified using the OptEIA™ ELISA kit (BD Pharmingen).

Study of Arachidonic Acid (AA) Metabolism (FIGS. 4A, 4B, 4C):

HaCaT keratinocytes were incubated in 24-well plates in the presence of 1 µCi [$^3$H]AA for 18 hours under an atmosphere of 5% $CO_2$. To test the capacity of PUFAs to modulate the inflammatory response of keratinocytes, [$^3$H]-labeled HaCaT cells are pretreated with PUFAs for 24 hours, rinsed and then stimulated by 500 nM PMA and 1 µM A23187 for 5 hours. [$^3$H]AA and metabolites released by the HaCaT cells in the culture medium are extracted by column chromatography. The eluate is evaporated under $N_2$. The dry residue is taken up in methanol and deposited on thin-layer silica plates activated beforehand for 1 hour at 100° C. The developing solvent is the organic phase of the mixture ethyl acetate/water/isooctane/acetic acid (110:100:50:20, v/v). [$^3$H]AA and metabolites (6-keto-prostaglandin $F_{1\alpha}$, 6k-$PGF_{1\alpha}$; prostaglandin (PG) F$\alpha$E2$D_2$; thromboxane (TX) $B_2$, leukotrienes (LT) $B_4$, $C_4$, $D_4$) are identified by a Berthold TLC scanner.

Figure 3:
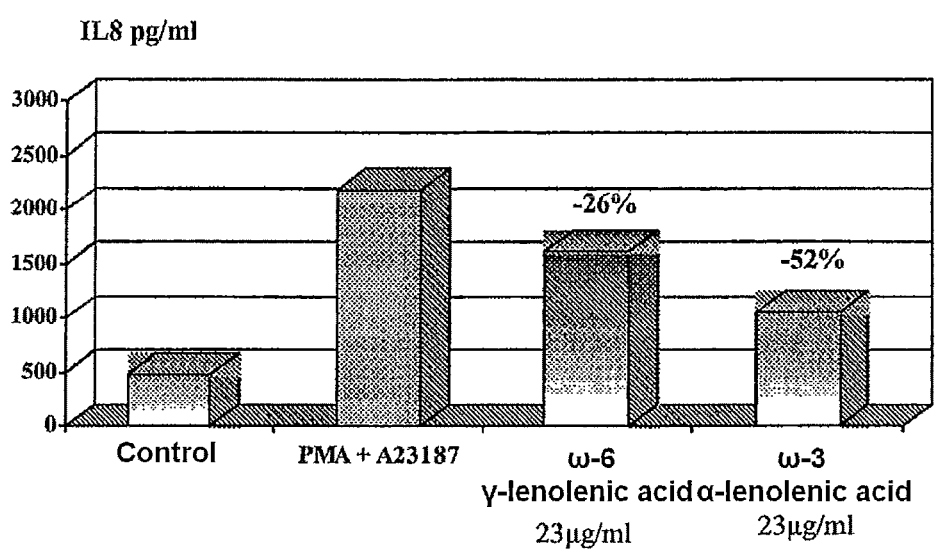
FIG. 3: Activity of PUFAs on the release of interleukin 8 by human HaCaT keratinocytes stimulated by PMA/A23187 (proinflammatory agents).

Thus, FIG. 3 shows the activity of certain PUFAs on the release of interleukin 8 (IL-8) by HaCaT human keratinocytes stimulated by PMA/A23187. An inhibitory effect on the IL-8 secretion of stimulated keratinocytes is clearly shown for γ-linolenic acid and particularly for α-linolenic acid.

Figure 4A:
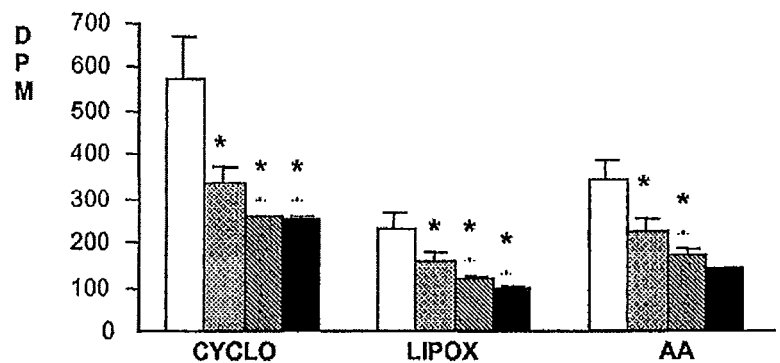
FIGS. 4A, 4B and 4C: Effects of PUFAs on the production of eicosanoids (CYCLO: cyclooxygenase metabolites, LIPOX: lipoxygenase metabolites, AA: arachidonic acid) during an inflammatory response induced by PMA/A23187. The white columns represent the control (a reaction medium without PUFAs); the light gray columns correspond to the activity of 2.3 µg/ml PUFA; the dark gray columns correspond to the activity of 11.5 µg/ml PUFA; and the black columns correspond to the activity of 23 µg/ml PUFA.
Figure 4B:
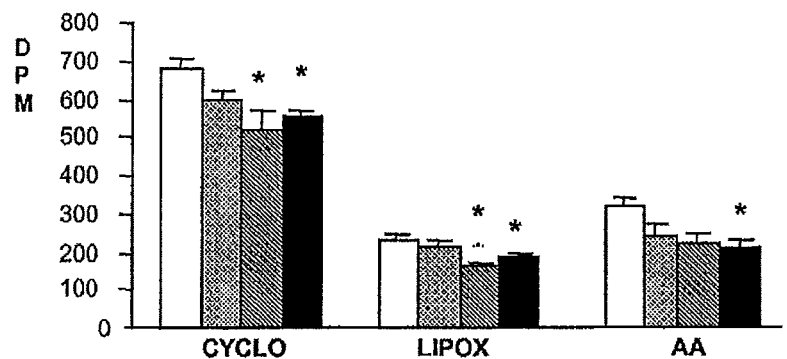
Figure 4C:
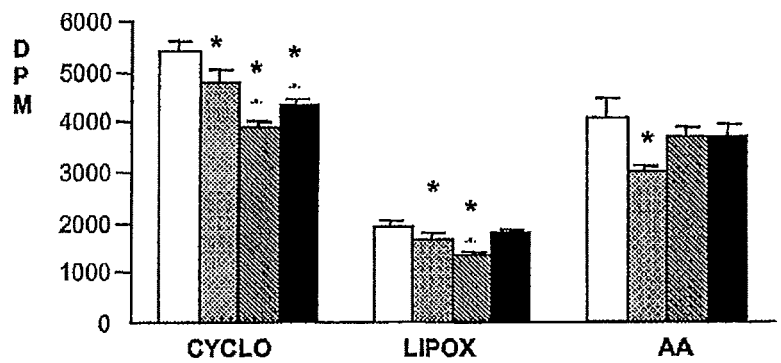

Similarly, pre-incubation of keratinocytes with a PUFA such as α-linolenic acid, stearidonic acid or linoleic acid significantly inhibits the release of arachidonic acid and also the release of cyclooxygenated and lipoxygenated metabolites of the inflammatory cascade (FIGS. 4A, 4B and 4C).

Thus, all of the results obtained confirm the anti-inflammatory activity of ω-3 or ω-6 polyunsaturated fatty acids and in particular α-linolenic acid.

The compounds according to the invention can thus be used to treat acne. Since the etiological pattern of seborrheic dermatitis has similarities with that of acne, the compounds of the invention can potentially also be used to treat seborrheic dermatitis. Indeed, the microorganism at the origin of the inflammatory response in the context of this pathology, *Malassezia*, secretes lipases (DeAngelis Y M et al. J Invest Dermatol. 2007; 127: 2138-46) on the scalp which can also be used to release the two active agents, the alkanediol with antifungal properties and the PUFA such as α-linolenic acid with anti-inflammatory properties. Moreover, certain fatty acids such as linoleic acid are activators of nuclear PPARα receptors, which exert a marked sebum control effect (Downie M M et al. Br J Dermatol. 2004; 151: 766-75). Thus, diol-linoleic acid conjugates can be used in particular to limit seborrhea in various indications such as acne and seborrheic dermatitis.

The invention claimed is:

1. A compound of the following general formula (I):

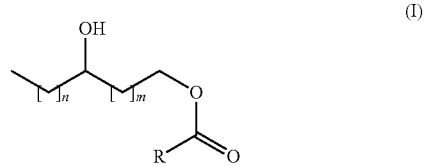

wherein:
n is an integer between 1 and 15,
m is 0, 1, 2 or 3, and
R is the hydrocarbon chain of a polyunsaturated fatty acid selected from omega-3 and omega-6 polyunsaturated fatty acids.

2. The compound according to claim 1, wherein n is between 1 and 10.

3. The compound according to claim 2, wherein a is 1, 2, 3, 4 or 5.

4. The compound according to claim 1, wherein m is 0 or 1.

5. The compound according to claim 1, wherein the polyunsaturated fatty acid is selected from α-linolenic acid, stearidonic acid, eicosatrienoic acid, eicosatetraenoic acid, eicosapentaenoic acid, docosapentaenoic acid, docosahexaenoic acid, tetracosapentaenoic acid, tetraeosahexaenoic acid, linoleic acid, γ-linolenic acid, eicosadienoic acid, dihomo-γ-linolenic acid, arachidonic acid, docosatetraenoic acid, docosapentaenoic acid, adrenic acid and calendic acid.

6. The compound according to claim 1, selected from the following molecules:

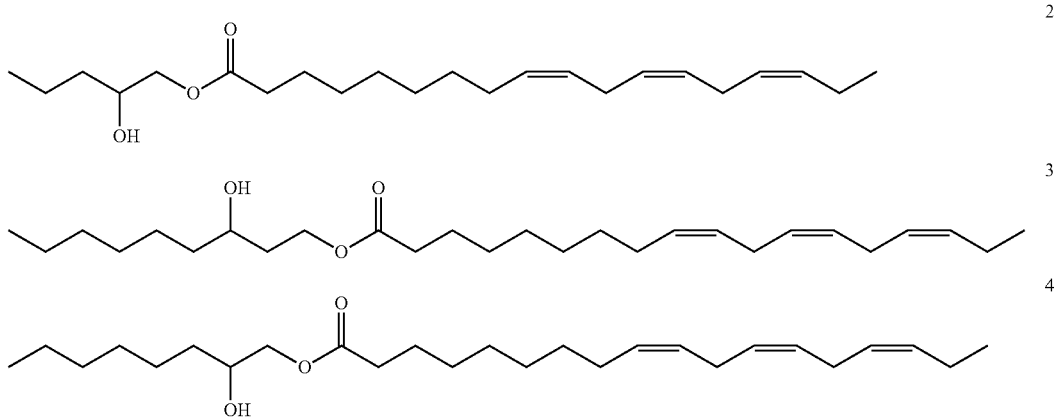

-continued

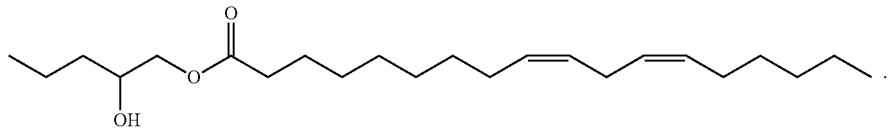

7. A method for treating acne or sebhorrheic dermatitis comprising the administration to a person in need thereof of en effective amount of a compound of formula (I) according to claim 1.

8. A pharmaceutical or cosmetic composition comprising at least one compound of the formula (I) according to claim 1 in combination with at least one pharmaceutically or cosmetically acceptable excipient.

9. The pharmaceutical or cosmetic composition according to claim 8, comprising 0.01% to 10% by weight of the said one or more compounds of the formula (I) compared to the total weight of the composition.

10. A method for the cosmetic treatment of acne or seborrheic dermatitis comprising the application on the skin of a cosmetic composition according to claim 8.

11. A method for preparing a compound of the formula (I) according to claim 1 by coupling a polyunsaturated fatty acid selected from omega-3 and omega-6 fatty acids, whose carboxylic acid function is in free or activated form, and a diol of the following formula (II):

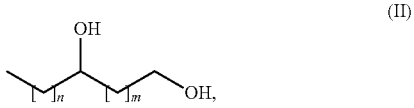

(II)

wherein n is an integer between 1 and 15, and m is 0, 1, 2 or 3.

12. The method according to claim 11, wherein the coupling reaction is carried out from the polyunsaturated fatty acid, whose carboxylic acid function is in free form, in the presence of a coupling agent selected from the group consisting of diisopropylcarbodiimide, dicyclohexylcarbodiimide, 1-(3-dimethylaminopropyl)-3-ethylcarbodiimide hydrochloride, carbonyldiimidazole, 2-H-benzotriazole-1-yl)-1,1,3,3,-tetramethyluronium hexafluorophosphate, 2-(1H-benzotriazole-1-yl)-1,1,3,3-tetramethyluronium tetrafluoroborate and O-(7-azobenzotriazol-1-yl)-1,1,3,3-tetramethyluronium hexafluorophosphate, optionally combined with a coupling auxiliary selected from the group consisting of N-hydroxysuccinimide, N-hydroxybenzotriazole, 3,4-dihydro-3-hydroxy-4-oxo-1,2,3-benzotriazole, 1-hydroxy-7-azabenzotriazole, dimethylaminopyridine and N-hydroxysulfosuccincmide.

13. The method according to claim 12, wherein the coupling agent is 1-(3-dimethylaminopropyl)-3-ethylcarbodiimide hydrochloride and the coupling auxiliary is dimethylaminopyridine.

14. The method according to claim 11, wherein the coupling reaction is carried out from the polyunsaturated fatty acid, whose carboxylic acid function is activated in the form of an acid chloride.

15. The compound according to claim 5, wherein the polyunsaturated fatty acid is selected from α-linolenic acid, stearidonic acid and linoleic acid.

16. The pharmaceutical or cosmetic composition according to claim 9, comprising 0.1% to 1% by weight of the said one or more compounds of the formula (I) compared to the total weight of the composition.

17. The method according to claim 11, wherein n is an integer between 1 and 10.

18. The method according to claim 11, wherein m is 0 or 1.

19. The method according to claim 14, wherein the coupling reaction is carried out from the polyunsaturated fatty acid, whose carboxylic acid function is activated in the form of an acid chloride, in the presence of pyridine and dimethylaminopyridine.

* * * * *